US012661481B2

(12) United States Patent
Farrissey

(10) Patent No.: US 12,661,481 B2
(45) Date of Patent: Jun. 23, 2026

(54) BALLOON OCCLUSION CATHETER

(71) Applicant: Crannmed Limited, County Galway (IE)

(72) Inventor: Liam Farrissey, County Galway (IE)

(73) Assignee: CrannMed Limited, Galway (IE)

( * ) Notice: Subject to any disclaimer, the term of this patent is extended or adjusted under 35 U.S.C. 154(b) by 792 days.

(21) Appl. No.: 17/414,720

(22) PCT Filed: Dec. 21, 2019

(86) PCT No.: PCT/IB2019/001420
§ 371 (c)(1),
(2) Date: Jun. 16, 2021

(87) PCT Pub. No.: WO2020/128633
PCT Pub. Date: Jun. 25, 2020

(65) Prior Publication Data
US 2022/0062599 A1      Mar. 3, 2022

Related U.S. Application Data

(60) Provisional application No. 62/874,161, filed on Jul. 15, 2019, provisional application No. 62/857,528, (Continued)

(51) Int. Cl.
*A61M 25/00*      (2006.01)
*A61M 25/10*      (2013.01)
(Continued)

(52) U.S. Cl.
CPC .... *A61M 25/0009* (2013.01); *A61M 25/0045* (2013.01); *A61M 25/1006* (2013.01); (Continued)

(58) Field of Classification Search
CPC .......... A61M 25/1034; A61M 25/1006; A61M 2025/1061; A61M 2025/0047; (Continued)

(56) References Cited

U.S. PATENT DOCUMENTS 5,342,386 A      8/1994  Trotta
5,603,991 A  *   2/1997  Kupiecki .......... A61M 25/0009
                                                     427/430.1
(Continued)

FOREIGN PATENT DOCUMENTS

CA          2029489 A1      5/1991
CN      104093381 A  *  10/2014  ............. A61F 2/966
(Continued)

OTHER PUBLICATIONS

First Office Action issued in corresponding Chinese Patent Application No. 201980084528.2, dated Jul. 29, 2022, with English translation.
(Continued)

*Primary Examiner* — Courtney B Fredrickson
*Assistant Examiner* — Kayla M. Turkowski
(74) *Attorney, Agent, or Firm* — Morgan, Lewis & Bockius LLP

(57)      ABSTRACT

A balloon catheter includes an outer tube that has an inner surface and an inflation lumen and an inner tube that is disposed within the inflation lumen. The balloon catheter also includes a collar that has a proximal end coupled to a distal end of the outer tube, and a distal end. The collar is coupled to an edge of the distal end or the inner surface of the outer tube. The balloon catheter further includes a luminal space, which is defined by a space between the outer surface of the inner tube and the collar, and a balloon. The balloon has a proximal end coupled to the collar and a distal end coupled to the inner tube.

32 Claims, 4 Drawing Sheets

Related U.S. Application Data filed on Jun. 5, 2019, provisional application No. 62/783,821, filed on Dec. 21, 2018.

(51) Int. Cl.
    *B05D 3/10*        (2006.01)
    *B05D 7/22*        (2006.01)

(52) U.S. Cl.
    CPC ........... *A61M 25/1034* (2013.01); *B05D 3/10* (2013.01); *A61M 2025/0042* (2013.01); *A61M 2025/1061* (2013.01); *A61M 2205/0222* (2013.01); *A61M 2205/0238* (2013.01); *B05D 7/22* (2013.01); *B05D 7/225* (2013.01); *B05D 2254/04* (2013.01)

(58) Field of Classification Search
    CPC .. A61M 2205/0222; A61M 2205/0238; A61M 2025/0048; A61M 25/1009; A61M 25/1025
    See application file for complete search history.

(56) References Cited

U.S. PATENT DOCUMENTS

| | | | | |
|---|---|---|---|---|
| 5,695,467 | A | 12/1997 | Miyata | |
| 6,287,285 | B1 * | 9/2001 | Michal | A61L 29/048 424/422 |
| 6,458,867 | B1 * | 10/2002 | Wang | A61F 2/966 523/105 |
| 6,596,217 | B1 * | 7/2003 | Davis-Lemessy | B29C 65/68 264/483 |
| 7,892,201 | B1 * | 2/2011 | Laguna | A61M 25/1034 604/96.01 |
| 9,550,046 | B1 * | 1/2017 | Allen | A61M 25/1034 |
| 2004/0059290 | A1 | 3/2004 | Palasis | |
| 2005/0038468 | A1 * | 2/2005 | Panetta | A61M 25/104 606/200 |
| 2005/0055044 | A1 * | 3/2005 | Kangas | A61L 29/145 606/194 |
| 2005/0137458 | A1 * | 6/2005 | Sakamoto | A61M 25/0662 600/116 |
| 2005/0187603 | A1 | 8/2005 | Eldenschink et al. | |
| 2011/0009942 | A1 * | 1/2011 | Gregorich | A61F 2/954 623/1.11 |
| 2012/0158035 | A1 * | 6/2012 | Schaeffer | A61M 25/104 606/194 |
| 2012/0232479 | A1 * | 9/2012 | Vo | A61M 25/0053 604/524 |
| 2014/0163367 | A1 * | 6/2014 | Eskuri | A61M 5/007 604/523 |
| 2022/0267572 | A1 * | 8/2022 | Iwasaki | B32B 25/18 |

FOREIGN PATENT DOCUMENTS

| | | | | |
|---|---|---|---|---|
| CN | 105311730 | A | 2/2016 | |
| CN | 205698849 | U | 11/2016 | |
| DE | 68928881 | T2 | 8/1999 | |
| EP | 1243284 | A1 | 9/2002 | |
| JP | 2002153560 | A | 5/2002 | |
| NL | 1008178 | C2 | 8/1999 | |
| WO | WO-9400170 | A1 * | 1/1994 | ......... A61M 25/104 |

OTHER PUBLICATIONS

International Search Report issued in corresponding Chinese Patent Application No. 201980084528.2, dated Jul. 20, 2022, with English translation.

International Preliminary Report on Patentability dated Jul. 1, 2021 for International Patent Application No. PCT/IB2019/001420, 11 pages.

International Search Report and Written Opinion dated Jul. 30, 2020 for International Patent Application No. PCT/IB2019/001420, 15 pages.

\* cited by examiner

100

100

BALLOON OCCLUSION CATHETER

CROSS REFERENCE TO RELATED APPLICATIONS

This application is a U.S National Phase of International Application No. PCT/IB2019/001420 filed on Dec. 21, 2019, which claims the benefit of U.S. Provisional Patent Application No. 62/783,821 filed Dec. 21, 2018 entitled "A Tube Having An Interior Lubricious Coating and Systems and Methods of Applying the Same", U.S. Provisional Patent Application No. 62/857,528 filed Jun. 5, 2019 entitled "Balloon-Occluded Transarterial Chemoembolization Device", and U.S. Provisional Patent Application No. 62/874,161 filed Jul. 15, 2019 entitled "Balloon Occlusion Microcatheter", each of which is incorporated by reference herein in their entirety.

FIELD OF THE INVENTION

The present invention generally relates to a balloon occlusion catheter, and more particularly, to a balloon occlusion catheter for inflating a balloon within a blood vessel to isolate a target vascular target or change the hemodynamic pressures around a vascular target

BACKGROUND OF THE INVENTION

Catheters are a thin tube made from medical grade materials that are inserted in the body to perform a broad range of functions. Catheters may be commonly used to dilate blood vessels, occlude blood vessels, or deliver and distribute fluids and/or particles throughout the body of a patient to a target site. Catheters can be designed with a small enough outer diameter to enter the blood vessels of a human body to reach a target tissue or organ. However, delivery of fluids and/or particles to non-target areas can cause complications and potentially harm the patient. For example, delivery of chemotherapeutics or embolic particles to a non-targeted organ can result in significant injury and complications to the non-targeted organ, such as organ failure.

One method of targeting specific areas for drug delivery is by using balloon catheters. These catheters can be commonly used to delivery fluids, therapeutics, and embolic particles to targeted tissues within the human body. These catheters include balloons to assist in dilating the delivery vessel, blocking fluid flow, and/or isolating areas of the body to prevent delivery to other non-targeted areas of the body. The balloons must be inflated using a lumen within the catheter. The larger the diameter of the lumen, the faster the balloon can be inflated and deflated. However, using a balloon with the catheter may result in a decreased outer diameter of the catheter since the balloon must sit along the circumference of the catheter without increasing the overall outer diameter of the device. Further, many catheters include inner tubes for delivery of fluids and particles. The inner tubes must have an inner diameter, which is maximized to allow for delivery of larger embolic particles. However, decreasing the overall diameter of the catheter results in a slower inflation rate of the balloon. Further, a decrease of the inner diameter of the inner tube may prevent the delivery of larger particles.

BRIEF SUMMARY OF THE INVENTION

In one embodiment, there is a balloon catheter that includes an outer tube that includes a distal end, an inner surface and an inflation lumen, an inner tube disposed within the inflation lumen of the outer tube, the inner tube includes an outer surface and an inner lumen, a collar that has a proximal end and a distal end, the proximal end coupled to a distal end of the outer tube, wherein the collar couples to an edge of the distal end or the inner surface of the outer tube, a luminal space defined by a space between the outer surface of the inner tube and the collar, and a balloon that has a proximal end and a distal end, the proximal end of the balloon is coupled to the collar and the distal end is coupled to the inner tube.

In one embodiment, the collar includes a slot that extends radially around an outer circumference of the collar, wherein the collar is at least partially disposed around the outer surface of the inner tube and the inner tube partially extends through the slot when the inner tube is disposed within the inflation lumen of the outer tube. The slot may extend longitudinally throughout a majority of a length of the collar. In one embodiment, the slot extends radially approximately 110° around the outer circumference of the collar. In one embodiment, the slot is configured to allow the outer surface of the inner tube to move closer to an inner surface of the outer tube.

In one embodiment, the collar has an outer diameter that is smaller than an outer diameter of the outer tube. In one embodiment, the collar is comprised of nitinol.

In one embodiment, the outer tube is comprised of nitinol and includes a plurality of slots allowing the outer tube to bend. In one embodiment, a width of each of the plurality of slots decreases along the length of the outer tube from a proximal end of the outer tube to a distal end of the outer tube. In one embodiment, the outer diameter of the outer tube is substantially less than or equal to 0.040 inches.

In one embodiment, the inner tube includes an inner diameter having a diameter substantially greater than or equal to 0.020 inches. In one embodiment, the inner tube is comprised of PTFE inner layer, a metal braid reinforcement layer, and an outer Pebax jacket. In one embodiment, the catheter further includes an outer jacket disposed over a portion of the outer tube and a portion of the collar, wherein the outer jacket is configured to be disposed over a portion of the balloon.

In some embodiments, the inner tube is comprised of braided polyimide. In one embodiment, the inner tube has a wall thickness of approximately 0.003 inches. In one embodiment, the outer surface of the inner tube engages with the outer tube to lock the inner tube to the outer tube such that rotation of the outer tube causes rotation of the inner tube. The catheter includes an adhesive to lock the inner tube to the outer tube.

In one embodiment, in a deflated state, the balloon has an outer diameter substantially less than or equal to an outer diameter of the outer tube. In one embodiment, the balloon includes an interior space that is in fluid communication with the outer tube through the luminal space of the collar. In one embodiment, the balloon is inflated with an inflation medium directed into the interior space of the balloon through the luminal space.

In one embodiment, the catheter includes a coating solution deposited on the inner lumen. In one embodiment, the coating solution has a thickness between 1 μm and 25 μm. In one embodiment, the coating solution is biocompatible, hydrophilic, or hydrophobic. In one embodiment, the coating solution is heat cured between 50 and 90 degrees Celsius after deposition on the inner lumen. In one embodiment, the coating solution is cured using ultraviolet light after deposition on the inner lumen. In one embodiment, the coating solution is cured such that it adheres to the inner lumen of the inner tube. In one embodiment, the coating solution is heat cured for a duration of between 10 minutes and 2 hours. In one embodiment, the coating solution is diluted by varying dilution percentages between 0% and 50%. In one embodiment, a primer solution or a basecoat solution is used as an adhesion promoter between the inner lumen of the inner tube and the coating solution. In one embodiment, a cleaning solution is used to prepare the inner lumen of the inner tube for application of the coating solution. In one embodiment, the cleaning solution is saline or an equivalent.

Another embodiment of the present invention provides a balloon catheter that includes an outer tube that has an outer diameter and an inflation lumen, an inner tube disposed within the inflation lumen of the outer tube, the inner tube has an inner lumen that includes a coating solution deposited on the inner lumen, a collar that has an outer diameter that is smaller than the outer diameter of the outer tube and a proximal end and a distal end, the proximal end coupled to the outer tube, and the collar has a slot wherein the inner tube is disposed within the slot and partially extends through the slot when the inner tube is disposed within the inflation lumen of the outer tube, and the collar includes a luminal space defined by a space between the inner tube and collar, and a balloon that has a proximal end and a distal end, wherein the proximal end is coupled to the collar and the distal end is coupled to the inner tube, and the balloon includes an interior space that is in fluid communication with the outer tube through the luminal space of the collar allowing the balloon to be inflated from a deflated state to an inflated state.

BRIEF DESCRIPTION OF THE SEVERAL VIEWS OF THE DRAWINGS

The following detailed description of embodiments of the balloon occlusion catheter will be better understood when read in conjunction with the appended drawings of exemplary embodiments. It should be understood, however, that the invention is not limited to the precise arrangements and instrumentalities shown.

DETAILED DESCRIPTION OF THE EXEMPLARY EMBODIMENTS OF THE INVENTION

Figure 1A:
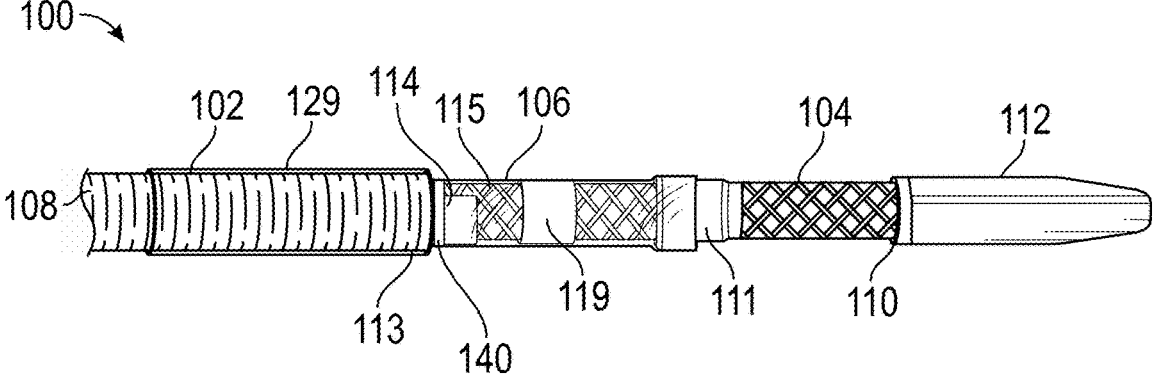
FIG. 1A is a side view of a balloon catheter in accordance with a first exemplary embodiment of the present invention shown with the balloon in a deflated state.

Catheters have been used to deliver fluids and particles to target sites, such as those disclosed in U.S. Pat. No. 9,550, 046, which is hereby incorporated by reference in its entirety. Catheters may be used with an inflatable balloon to deliver drugs to a target site. The balloon may be inflated to occlude or dilate the vessel during delivery. The outer catheter and inner catheter may be coaxially disposed to form annular lumen. The annular lumen may be in fluid communication with the interior of balloon to inflate and deflate balloon. The size of annular lumen may therefore dictate the inflation rate of balloon, because more inflation medium can enter the interior space of balloon when annular lumen is larger.

Exemplary embodiments of the present invention provide for an improved catheter as shown in FIGS. 1A-8. In use, catheter 100 may include an outer tube, and inner tube within the outer tube. Catheter 100 may be configured to deliver fluid and/or particles to a target site, occlude a blood vessel, dilate a blood vessel, view the interior of an organ or vessel, and/or assist in surgery. The inner tube of catheter 100 may be configured to be used with a variety of fluids and particles of various sizes. In certain situations, catheter 100 may include a balloon as it may be desirable to occlude or dilate a vessel for delivery of necessary particles to a targeted area within the body. For example, in delivering chemotherapeutics to a target organ, it may be necessary to occlude the artery to prevent the chemotherapeutics from being delivered downstream to other organs. Catheter 100 may be configured to quickly inflate the balloon without reducing the diameter of the inner tube, thus allowing for the delivery of larger particles at high flow rates. For example, it is optimal to inflate the balloon in less than approximately 10 seconds, less than approximately 20 seconds, less than approximately 30 seconds, less than approximately 40 seconds, less than approximately 50 seconds, or less than approximately 60 seconds. Further, catheter 100 may be configured to allow the balloon to rapidly deflate to minimize the time that catheter 100 is in the blood vessel. For example, the balloon may deflate in less than approximately 10 seconds, less than approximately 20 seconds, less than approximately 30 seconds, less than approximately 40 seconds, less than approximately 50 seconds, or less than approximately 60 seconds. In a preferred embodiment, the balloon may achieve inflation in between approximately 10-15 seconds, and may achieve deflation in approximately 5-10 seconds.

Referring to FIGS. 1A-8, catheter 100 may include outer tube 102, inner tube 104, balloon 106, and collar 114. Outer tube 102 may include proximal end 108 and distal end 113, and may extend longitudinally from proximal end 108 to distal end 113. Outer tube 102 may house inner tube 104, such that inner tube 104 is at least partially disposed within outer tube 102. Inner tube 104 may include proximal end 115 and distal end 110. Proximal end 115 may extend proximally and may be disposed under outer tube 102. An end of proximal end 115 may be embedded within a bifurcated luer. Distal end 110 may extend distally and may be disposed under distal tip 112. Catheter 100 may include collar 114, which may be coupled to distal end 113 of outer tube 102. Catheter 100 may further include balloon 106, which may be coupled to collar 114 and proximal end 115 of inner tube 104. Balloon 106 may be configured to inflate and deflate. When inflated, balloon 106 may include interior space 117. During inflation, collar 114 may be partially disposed within interior space 117. Balloon 106 may be inflated by an inflation medium, which may flow through outer tube 102 into interior space 117 of balloon 106.

Referring to FIGS. 1A-8, catheter 100 may include outer tube 102. Outer tube 102 may be comprised of a shape memory alloy, such as nitinol (NiTi). In one embodiment, outer tube 102 is comprised of laser cut nitinol. Outer tube 102 may be comprised of nitinol reinforced polymer braid and/or coil, wire formed cable, or stainless steel reinforced braid and/or coil. Outer tube 102 may include plurality of depressions 136. Plurality of depressions 136 may be configured to increase the flexibility of outer tube 102. Plurality of depressions 136 may be disposed along the length of outer tube 102, from proximal end 108 to distal end 113. In one embodiment, plurality of depressions 136 are laser cut and each have a width of the laser beam. For example, plurality of depressions 136 may be cut with a laser having a laser beam between approximately 10-35 microns resulting in the plurality of depressions 136 each having a width between approximately 10-35 microns. In some embodiments, the width of each of the plurality of depressions 136 is generally constant. In other embodiments, the width of each of the plurality of depressions 136 decreases along the length of outer tube 102 from proximal end 108 to distal end 113 of outer tube 102. In some embodiments, depressions 136 extend only partially through the wall of the tube. In other embodiments depressions 136 extend entirely through outer tube 102, thereby forming slots. In some embodiments, outer tube 102 may include a combination of a plurality of depressions and a plurality of slots along the longitudinal axis of outer tube 102.

Figure 5A:
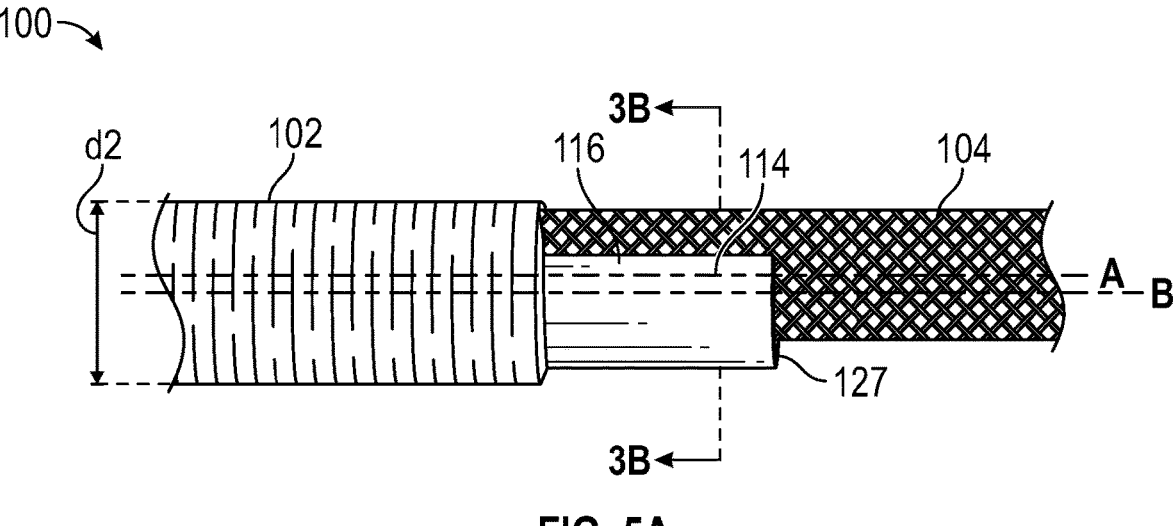
FIG. 5A is an enlarged side view of the catheter of FIG. 1A shown with the balloon and outer jacket removed for purposes of viewing the collar in greater detail.
Figure 5B:
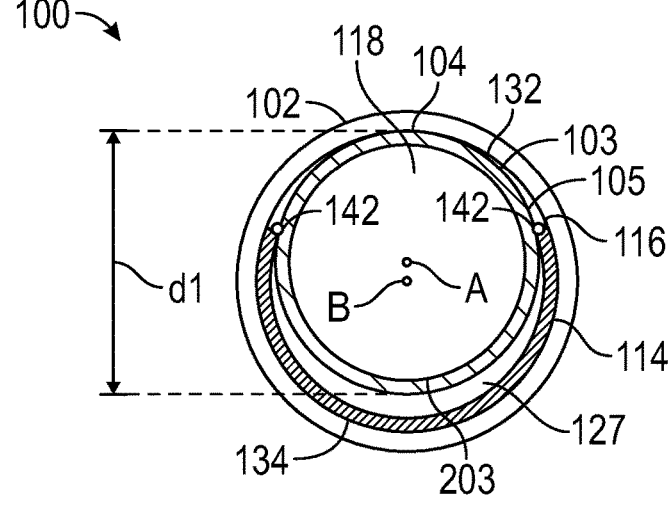
FIG. 5B is a cross sectional side view of the collar of FIG. 5A taken about a plane perpendicular to line A-A in FIG. 5A.

Referring to FIGS. 5A-B, outer tube 102 may include inner surface 103, outer diameter d2, and longitudinal axis B. Longitudinal axis B may extend the length of outer tube 102 through the center of outer tube 102. In one embodiment, outer diameter d2 is the maximum diameter of catheter 100. In one embodiment, outer diameter d2 may be minimized to allow for outer tube 102 to be placed in smaller vessels. For example, outer tube 102 may be sized such that catheter 100 is a microcatheter. Microcatheters are catheters that have a small outer diameter, thereby allowing them to enter blood vessels. For example, microcatheters typically have an outer diameter between approximately 0.02 inches and 0.08 inches. In some embodiments, outer diameter d2 is no greater than approximately 0.010 inches, no greater than approximately 0.020 inches, no greater than approximately 0.030 inches, no greater than approximately 0.040 inches, no greater than approximately 0.050 inches, no greater than approximately 0.060 inches, no greater than approximately 0.070 inches, no greater than approximately 0.080 inches, no greater than approximately 0.090 inches, or no greater than approximately 0.100 inches. In a preferred embodiment, outer diameter d2 is no greater than approximately 0.040 inches. For example, outer diameter d2 may be approximately 0.0375 inches.

Figure 1B:
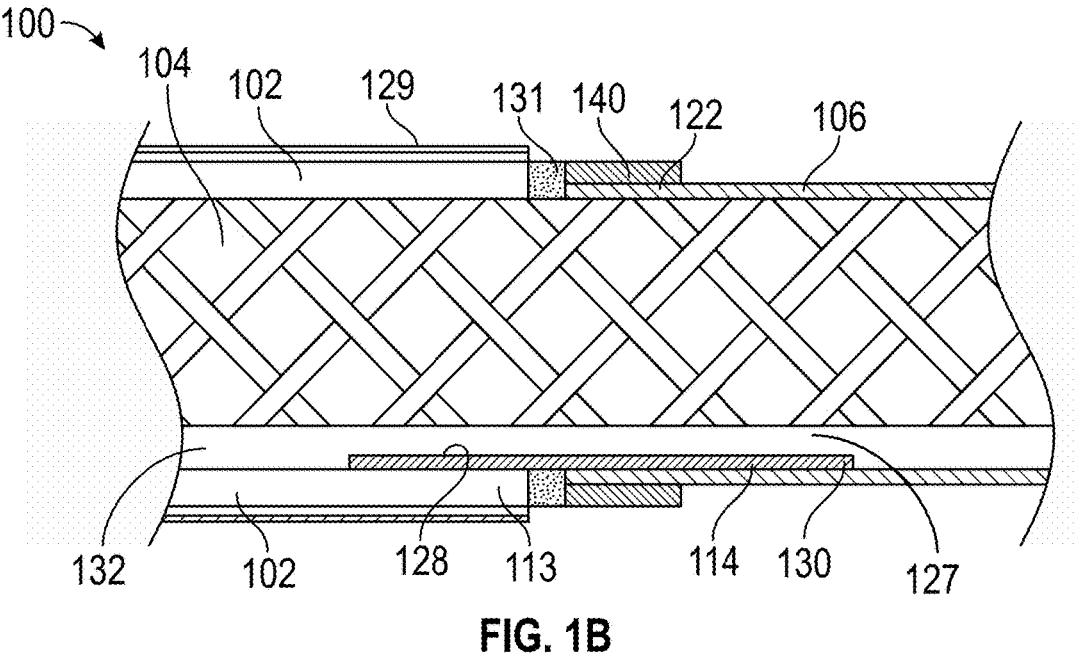
FIG. 1B is cross-section view of the balloon catheter of FIG. 1A.
Figure 2:
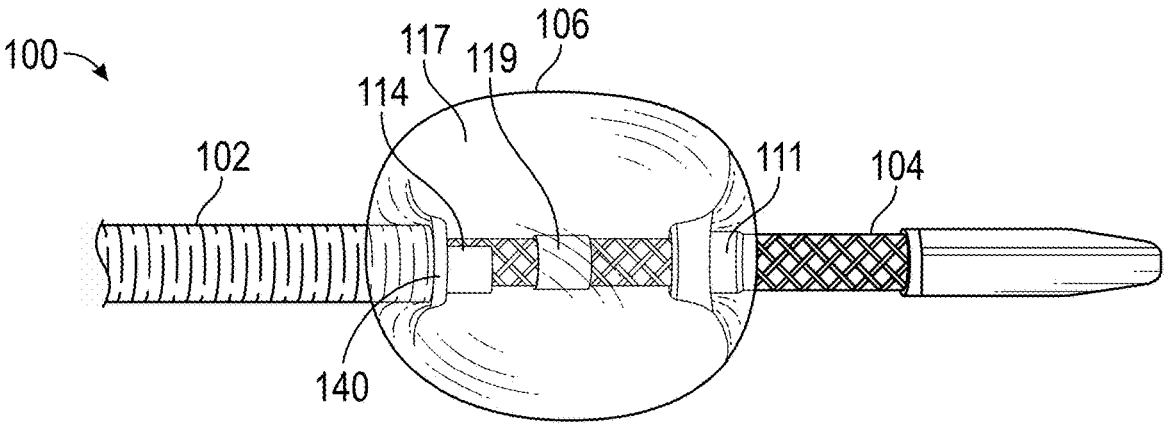
FIG. 2 is a side view of the balloon catheter of FIG. 1A shown with the balloon in an inflated state and an outer jacket removed.

Referring to FIGS. 1B and 5B, outer tube 102 may further include inflation lumen 132, which may be disposed within the interior of outer tube 102. Inflation lumen 132 may extend a majority of the length of catheter 100 and may be the space between inner tube 104 and outer tube 102. Inflation lumen 132 may include an inner diameter, which may be maximized to maximize the size of inner tube 104, which is disposed within inflation lumen 132. In some embodiments, the inner diameter of inflation lumen 132 is no greater than approximately 0.010 inches, no greater than approximately 0.020 inches, no greater than approximately 0.030 inches, no greater than approximately 0.040 inches, no greater than approximately 0.050 inches, no greater than approximately 0.060 inches, no greater than approximately 0.070 inches, no greater than approximately 0.080 inches, no greater than approximately 0.090 inches, or no greater than approximately 0.100 inches. In one embodiment, the inner diameter is approximately 0.0335 inches.

Referring to FIGS. 1A-5B, catheter 100 may include inner tube 104, which may be disposed within inflation lumen 132 of outer tube 102. Inner tube 104 may include longitudinal axis A, outer surface 105, and inner lumen 118. Longitudinal axis A may extend the length of inner tube 104 through the center of inner lumen 118. Inner lumen 118 may have inner diameter d1. Inner lumen 118 may be sized to deliver particles and/or particles to a target area. For example, inner diameter d1 of inner lumen 118 may be sized to house and deliver contrast, embolic particles or coils, medicament or particles to a target site, and/or surgical tools. Inner lumen 118 may be configured to deliver particles sized approximately 0.005 inches, 0.010 inches, 0.015 inches, 0.020 inches, 0.025 inches, or 0.030 inches. In a preferred embodiment, inner lumen 118 is configured to delivery particles sized approximately 500 μm in diameter and coils up to 0.018 inches in diameter along with other interventional accessories measuring up to 0.018 inches in outside diameter. Inner diameter d1 of inner lumen 118 may be maximized to deliver large particles to a target area, without increasing the overall profile of catheter 100, such as outer diameter d2 of outer tube 102. Further, maximizing the size of inner lumen 118 allows for the fluids and particles to be injected at high flow rates. For example, maximizing the size of inner lumen 118 allows for the delivery of particles and/or fluids at a flow rate of between approximately 1 ml/second and 10 ml/second. In some embodiments, inner diameter d1 is at least 0.010 inches, 0.020 inches, 0.030 inches, 0.040 inches, 0.050 inches, 0.060 inches, 0.070 inches, 0.080 inches, 0.090 inches, or 0.100 inches. In a preferred embodiment, inner diameter d1 is 0.020 inches.

In some embodiments, inner tube 104 may be comprised of polytetrafluoroethylene (PTFE). Inner tube 104 may be a PTFE lined braided construction. In other embodiments, inner tube 104 may be braided polyimide. Inner tube 104 may be comprised of nitinol reinforced polymer braid and/or coil, wire formed cable, or stainless steel reinforced braid and/or coil. In some embodiments, inner tube 104 includes an outer jacket comprised of a polyether block amide, such as Pebax, and a metal braid reinforcement layer. The outer jacket of inner tube 104 may assist in inner tube 104 resisting kinking or bending. In one embodiment, the outer jacket assists in increasing the burst pressure of inner tube 104 such that inner tube 104 can receive fluids being injected at a pressure up to approximately 1200 PSI without causing damage to inner tube 104. In certain applications, it may be advantageous to minimize the thickness of the wall of inner tube 104. The thinner the wall of inner tube 104, the more space available for inflation lumen 132. Inner tube 104 may have a wall thickness no greater than approximately 0.001 inches, no greater than approximately 0.002 inches, no greater than approximately 0.003 inches, no greater than approximately 0.004 inches, no greater than approximately 0.005 inches, no greater than approximately 0.010 inches, or no greater than approximately 0.050 inches.

In practice, inner tube 104 may be inserted into outer tube 102. In some embodiments, proximal end 108 of outer tube 102 may include a bifurcated luer. The bifurcated luer may allow simultaneous access to outer tube 102 and inner tube 104. The bifurcated luer may include an in-line lumen and an out-of-plane lumen. The in-line lumen may be configured to allow a guidewire or other therapeutic elements, such as embolization coils or embolic particles, to enter and exit catheter 100. The out-of-plane lumen may be configured to allow a syringe access to catheter 100 and luminal space 127 to inflate balloon 106. The bifurcated luer may include one arm allowing access to inner lumen 118 of inner tube 104 and a second arm allowing access to inflation lumen 132. In some embodiments, inner tube 104 being disposed within outer tube 102 may allow for inner tube 104 to be locked together with outer tube 102. Inner tube 104 may be locked with outer tube 102 due to inner tube 104 being disposed within collar 114. Locking inner tube 104 with outer tube 102 may allow for increased torque transmission from proximal end 108 to distal end 110. For example, when inner tube 104 is locked with outer tube 102 rotation of outer tube 102 results in rotation of inner tube 104. In some embodiments, the locking of inner tube 104 to outer tube 102 may be aided with the use of an adhesive or by welding.

Referring to FIGS. 1A and 1B, catheter 100 may include distal tip 112. In some embodiments, distal tip 112 may be coupled to distal end 110 of inner tube 104. Distal tip 112 may be made of a soft material to prevent damage to surrounding tissues. For example, distal tip 112 may be comprised of a soft material, such as 35 D Pebax with a radiopaque filler, to prevent distal end 110 of inner tube 104 from damaging vessels or other bodily tissues. Distal tip 112 including a radiopaque filler allows for distal tip 112 to be seen using traditional imaging techniques, such as X-ray.

Referring to FIGS. 1A-8, catheter 100 may include collar 114 for coupling the balloon to outer tube 102. In some embodiments, collar 114 does not extend over the outer surface of outer tube 102 to prevent increasing the outer diameter of catheter 100. Collar 114 may include proximal end 128 and distal end 130. Collar 114 may be laser cut nitinol. In other embodiments, collar 114 may be stainless steel, braid, reinforced polymer, or any other material that is capable of being bonded with nitinol. Proximal end 128 of collar 114 may be coupled to distal end 113 of outer tube 102. Proximal end 128 may be coupled to distal end 113 by welding, adhesive, friction-fit, or via threaded engagement. In some embodiments, proximal end 128 of collar 114 may overlap with outer tube 102 when collar 114 is coupled to outer tube 102. For example, proximal end 128 of collar 114 may be partially inserted into outer tube 102. In some embodiments, collar 114 may be coupled to inner surface 103 of outer tube 102. For example, collar 114 may be coupled to inner surface 103 of outer tube 102 such that outer tube 102 overlaps with collar 114. In some embodiments, collar 114 is coupled to distal end 113 of outer tube 102 in an edge-to-edge fashion via welding, such as butt welding, an adhesive, or any other type of coupling mechanism. Further, distal end 130 of collar 114 may be free and not coupled to another structure. For example, distal end 130 of collar 114 may not be coupled to another element and may reside within interior space 117 of balloon 106. In an alternative embodiment, collar 114 is integrally formed with outer tube 102.

Figure 7:
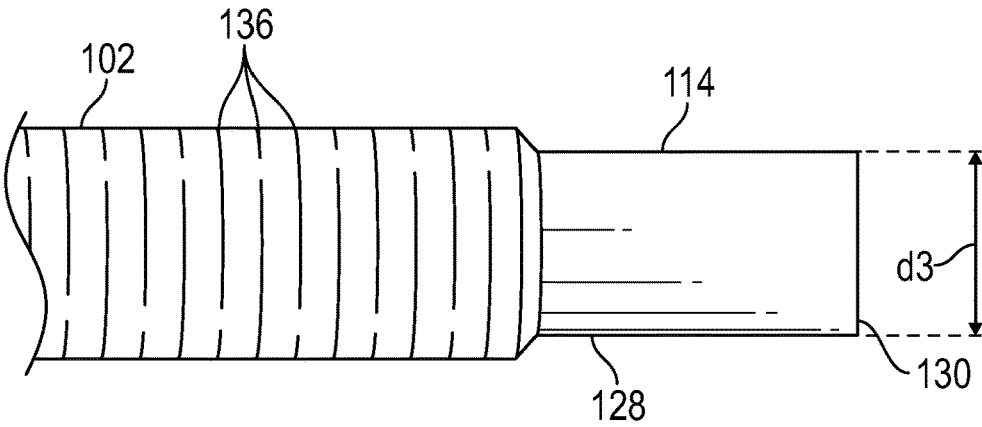
FIG. 7 is an enlarged bottom view of the catheter of FIG. 5A shown with the balloon and inner tube removed for purposes of viewing the collar in greater detail.

Referring to FIG. 7, collar 114 may include an inner diameter and outer diameter d3. The inner diameter may be approximately no greater than approximately 0.010 inches, no greater than approximately 0.020 inches, no greater than approximately 0.030 inches, no greater than approximately 0.040 inches, no greater than approximately 0.050 inches, no greater than approximately 0.060 inches, no greater than approximately 0.070 inches, no greater than approximately 0.080 inches, no greater than approximately 0.090 inches, or no greater than approximately 0.100 inches. In a preferred embodiment, the inner diameter of collar 114 is approximately 0.030 inches. Outer diameter d3 may be no greater than approximately 0.010 inches, no greater than approximately 0.020 inches, no greater than approximately 0.030 inches, no greater than approximately 0.040 inches, no greater than approximately 0.050 inches, no greater than approximately 0.060 inches, no greater than approximately 0.070 inches, no greater than approximately 0.080 inches, no greater than approximately 0.090 inches, or no greater than approximately 0.100 inches. In a preferred embodiment, outer diameter d3 may be approximately 0.032 inches. In one embodiment, outer diameter d3 may be smaller than outer diameter d2 of outer tube 102. In an alternative embodiment, outer diameter d3 is the same size as outer diameter d2. In some embodiments, outer diameter d3 is the same along the entire length of collar 114. In some embodiments, the presence of collar 114 does not increase the overall outer diameter of catheter 100. For example, catheter 100 including collar 114 coupled to outer tube 102 does not result in an increase in the overall outer diameter of catheter 100. In some embodiments, coupling collar 114 to outer tube 102 does not reduce the inner diameter of outer tube 102.

Referring to FIG. 5B, collar 114 may include adhesive 142. Adhesive 142 may be applied to outer surface 105 of inner tube 104 and collar 114 such that such that outer surface 105 adheres to collar 114, thereby locking inner tube 104 in position with outer tube 102.

Figure 8:
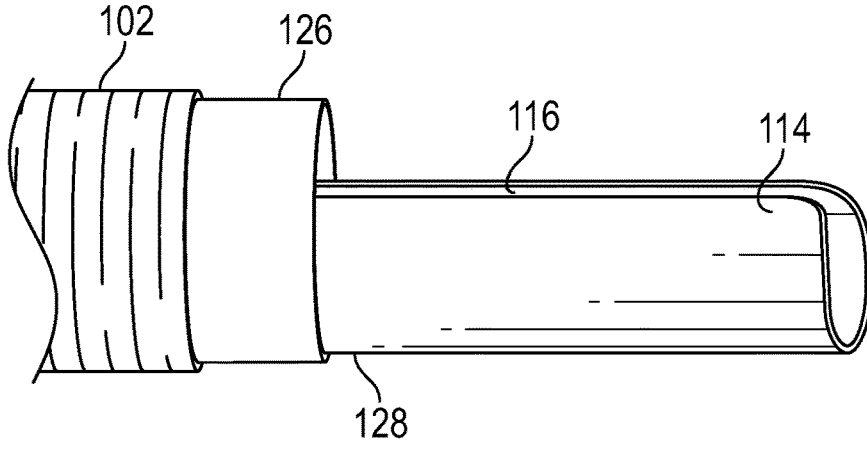
FIG. 8 is an enlarged side view of a balloon catheter in accordance with a second exemplary embodiment of the present invention with inner tube and balloon removed.

Referring to FIG. 8, outer tube 102 may include distal portion 126, which is a distal area of outer tube 102 that has an outer diameter less than outer diameter d2. Distal portion 126 may be coupled to outer tube 102 or may be a part of outer tube 102 having a reduced outer diameter d2. For example, distal portion 126 may be created by the removal of material from outer 102 via a laser such that distal end 113 of outer tube 102 is made thinner over the last 0.3 mm portion of outer tube 102. However, distal end 113 may be made thinner over the last approximately 0.1 mm, approximately 0.2 mm, approximately 0.4 mm, approximately 0.5 mm, or approximately 0.6 mm portion of outer tube. Distal portion 126 may be located at distal end 113 of outer tube 102, before collar 114. In one embodiment, distal portion 126 of outer tube 102 has a reduced diameter for a portion of distal end 113 of outer tube 102 before collar 114. In some embodiments, distal portion 126 may have a reduced diameter for between approximately 0.01 inches to 0.10, 0.03 inches to 0.08 inches, or 0.05 inches to 0.7 inches of distal end 113. In some embodiments, distal portion 126 is not laser cut for flexibility. Distal portion 126 may result in a decrease of outer diameter d2 by approximately 0.0015 inches. However, distal portion 126 may result in a decrease of outer diameter d2 by approximately 0.001 inches, 0.010 inches, 0.020 inches, 0.025 inches, 0.035 inches, or 0.050 inches. In some embodiments, distal portion 126 may be devoid of any depression or slots to limit flexing of distal portion 126.

Referring to FIG. 8, proximal end 128 of collar 114 may be coupled to distal portion 126. Proximal end 128 of collar 114 may be coupled to distal portion 126 via welding, an adhesive, soldering, or any other method of coupling desired. Proximal end 128 of collar 114 may be coupled to distal portion 126 and may include outer diameter d3, which may be less than distal portion 126, resulting in proximal end 128 having an additional distal portion when collar 114 is coupled to outer tube 102. For example, outer diameter d3 of collar 114 may have an additional reduction of between approximately 0.0015 inches to approximately 0.002 inches compared to distal portion 126 or outer diameter d3 of outer tube 102. Outer diameter d3 of collar 114 may be substantially the same from proximal end 128 to distal end 130.

Referring to FIGS. 5A-B and 8, collar 114 may include slot 116, which may extend circumferentially around outer circumference 134 of collar 114. Slot 116 may be a circumferential gap through the wall of collar 114 that extends longitudinally between proximal end 128 and distal end 130 of collar 114. Slot 116 may be cut into collar 114 and extend longitudinally from proximal end 128 to distal end 130. Slot 116 may be cut or formed into collar 114. In one embodiment, slot 116 is cut or formed into collar 114 via a laser. In some embodiments, slot 116 may be sized and shaped to allow inner tube 104 to sit within outer tube 102, locking inner tube 104 to outer tube 102. Slot 116 may allow inner tube 114 to axis shift upwards towards outer tube 102 thereby maximizing luminal space 127. In one embodiment, slot 116 may extend circumferentially approximately 110° around outer circumference 134. Slot 116 may extend circumferentially between approximately 10° to 350°, 30° to 320°, 60° to 290°, 90° to 270°, 120° to 240°, or 150° to 210°. In some embodiments, slot 116 extends circumferentially approximately 90°, 95°, 100°, 110°, 120°, 130°, 140°, 150°, 160°, 170°, or 180°. Slot 116 may be configured to allow for easier attachment of collar 114 to outer tube 102. For example, slot 116 allows for the easy placement of an adhesive or provides better access for welding collar 114 to outer tube 102.

Slot 116 may be configured to allow inner tube 104 to abut outer tube 102 such that outer surface 105 of inner tube 104 is adjacent to inner surface 103 of outer tube 102. For example, slot 116 may be configured to allow outer surface 105 of inner tube 104 to move closer to inner surface 103 of outer tube 102. Slot 116 may allow collar 114 to be at least partially disposed around outer surface 105 of inner tube 104 such that inner tube 104 partially extends through slot 116 when inner tube 104 is disposed within inflation lumen 132 of outer tube 102. In some embodiments, outer surface 105 of inner tube 104 may contact inner surface 103 of outer tube 102. Collar 114 having a step down or being coupled to distal portion 126 may allow for inner tube 104 to extend through slot 116 of collar 114 without increasing the overall diameter of catheter 100. This results in an increased area of luminal space 127. For example, during use, inner tube 104 may extend through slot 116 of collar 114 to increase the area of luminal space 127, and due to collar 114 having a step down from outer diameter d2, inner tube 104 extending through slot 116 does not increase the maximum diameter of catheter 100, or at least minimizes the increase, especially when balloon 106 is coupled catheter 100.

Referring to FIG. 5B, inner tube 104 partially extends through slot 116 such that outer surface 105 of inner tube 104 is adjacent to inner surface 103 of outer tube 102 to increase luminal space 127, which is defined by the space between outer surface 105 and collar 114. For example, slot 116 may allow longitudinal axis A of inner tube 104 to radially shift upwards away from longitudinal axis B of outer tube 102, towards inner surface 103 of outer tube 102 thereby increasing luminal space 127. In one embodiment, inner tube 104 is radially shifted upwards away from longitudinal axis B until it abuts inner surface 103 of outer tube 102 or is as close to inner surface of outer 102 as possible.

Figure 6:
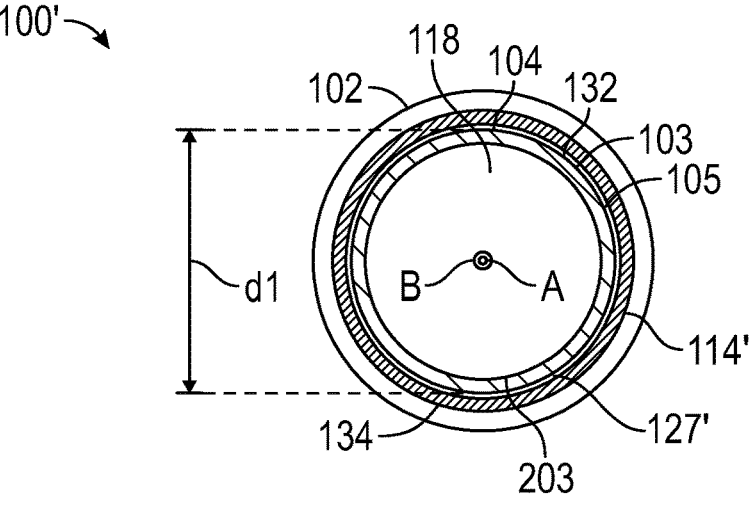
FIG. 6 is a cross sectional side view of the collar of FIG. 5A with the slot removed, taken about a plane perpendicular to line A-A in FIG. 5A.

FIG. 6 shows an embodiment of catheter 100' without slot 116 where inner tube 104 cannot radially shift towards inner surface 103 of outer tube 102. Without slot 116 (FIG. 6), the top of the inner tube 104 is not able to radially shift relative to outer tube 102 as it can with slot 116 (FIG. 5B). Due to the presence of slot 116, luminal space 127 in FIG. 5B is larger than luminal space 127' in FIG. 6. Luminal space 127 may be partially continuous with inflation lumen 132 such that material entered into inflation lumen 132 may flow through luminal space 127. Inner tube 104 may be disposed within slot 116 to maximize the area of luminal space 127. For example, inner tube 104 may be disposed within collar 114 such that inner tube 104 partially extends through slot 116, thereby maximizing luminal space 127. Slot 116 may be designed to minimize the amount of outer circumference 134 of collar 114 that needs to be removed to accommodate inner tube 104. In some embodiments, a reduction in outer diameter d3 of collar 114 does not cause a reduction of luminal space 127.

Referring to FIG. 6, collar 114' not including slot 116 may be advantageous as it still results in balloon 106 not increasing the overall outer diameter of catheter 100. For example, collar 114' may have reduced outer diameter d3 compared to outer diameter d2 of outer tube 102, allowing balloon 106 to couple to collar 114' without increasing outer diameter d2. This allows outer diameter d2 to be maximized. Further, even though luminal space 127' is smaller compared to the embodiment including slot 116 (FIG. 5B), collar 114' not having slot 116 may still allow for the inflation of balloon 106 via luminal space 127'. For example, luminal space 127' may still allow for the flow of an inflation medium to interior space 117 of balloon 106. This may be because luminal space 127' is only a single local narrowing within catheter 100. The flow of the inflation medium through inflation lumen 132 and out of luminal space 127' is heavily influenced by the overall space within inflation lumen 132 over the entire length of catheter 100. For example, by including collar 114', outer diameter d2 can be maximized resulting in an increase in the diameter of inflation lumen 132. This increase in diameter of inflation lumen 132 results in an increased flow rate of inflation medium flowing through inflation lumen 132.

Referring to FIGS. 1A-4, catheter 100 may include balloon 106. Balloon 106 may be comprised of a polymer such as polyethylene terephthalate, polypropylene, polystyrene, or polyurethane and may include proximal end 122 and distal end 124. In some embodiments, proximal end 122 of balloon 106 may be circumferentially coupled to collar 114 and distal end 124 may be circumferentially coupled to inner tube 104. For example, balloon 106 may be circumferentially coupled to collar 114 via an adhesive, support band 140, 140', or other coupling mechanism. In alternative embodiments, proximal end 122 of balloon 106 may be circumferentially coupled to outer tube 102. In some embodiments, distal end 124 of balloon 106 may be circumferentially coupled to junction 111. Junction 111 may be an area or material circumferentially disposed around inner tube 104. Proximal end 122 and distal end 124 of balloon 106 may be circumferentially coupled to collar 114 and junction 111, respectively, to circumferentially secure balloon 106 to catheter 100 and creating a sealed interior space 117 of balloon 106. Proximal end 122 of balloon 106 may be secured to collar 104 via an adhesive or a compressive heat shrink sleeve.

Figure 3:
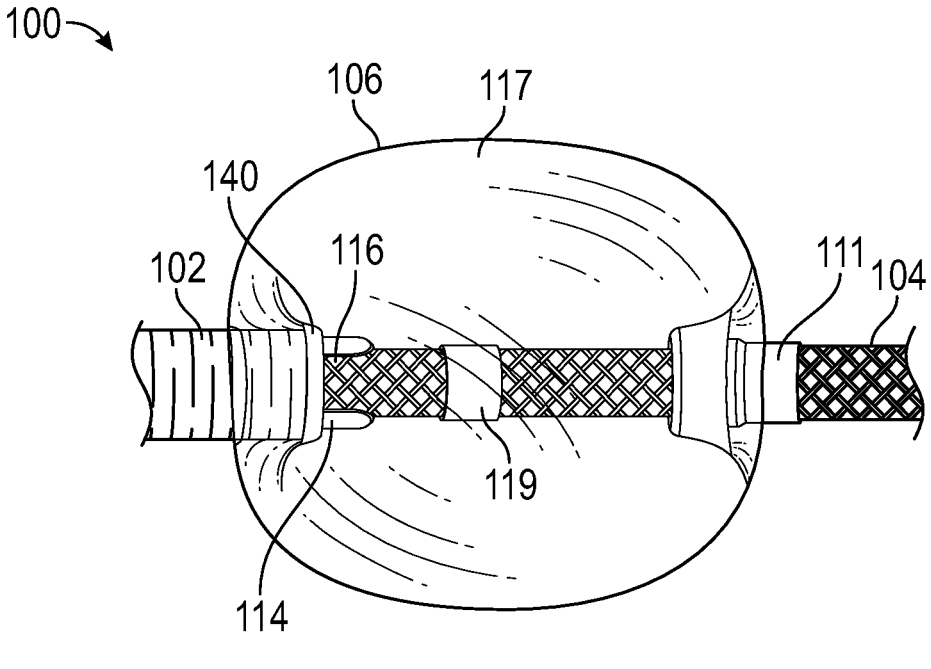
FIG. 3 is a top view of the balloon catheter of FIG. 1A shown with the balloon in an inflated state.
Figure 4:
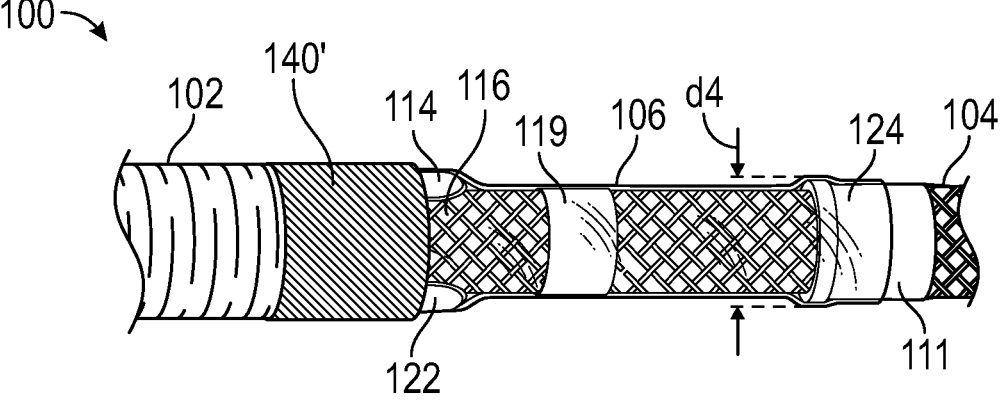
FIG. 4 is an enlarged top view of the balloon catheter of FIG. 1A shown with the balloon in a deflated state and with a thicker support band.

Referring to FIGS. 3-4, balloon 106 may have a deflated state (FIG. 4) and an inflated state (FIG. 3). In a deflated state, balloon 106 may have outer diameter d4, which may be less than or substantially equal to outer diameter d2 of outer tube 102. For example, when balloon 106 is deflated, the maximum diameter of catheter 100 may be substantially equal to outer diameter d2. In some embodiments, outer diameter d4 of balloon 106 may be greater than outer diameter d2 of outer tube 102, but still smaller than if catheter 100 did not include collar 114 or distal portion 126.

Referring to FIGS. 1A-4, in some embodiments, balloon 106 may include support band 140 that may be used to secure balloon 106 to catheter 100. For example, support band 140 may be separate element and may be used to assist in securing balloon 106 to collar 114, outer tube 102, and/or inner tube 104. However, in some embodiments, support band 140 may be a thicker portion of balloon 106. For example, support band 140 may be a band, a thread, a heat shrink jacket a clamp, or another circumferential restraining device. In some embodiments, support band 140 may be a wide band, such as support band 140' shown in FIG. 4. In some embodiments, support band 140 is integral with collar 114. Support band 140 may be used to strengthen the coupling of proximal end 122 to collar 114, outer tube 102, and/or distal end 124 to inner tube 124/junction 111. In some embodiments, support band 140 may assist in securing balloon 106 to distal portion 126 or collar 114 and may be configured to not increase the overall outer diameter of catheter 100. For example, support band 140, when circumferentially disposed around distal portion 126 or collar 114 to couple balloon 106 to distal portion 126 or collar 114, may increase the outer diameter of distal portion 126 or collar 114. However, since distal portion 126 and collar 114 have reduced outer diameters compared to outer diameter d2 of outer tube 102, the addition of support band 140 to distal portion 126 or collar 114 does not increase outer d2 diameter of outer tube 102. In some embodiments, an additional support bands may be used to couple balloon 106 to inner tube 104, junction 111, or other portions of catheter 100. In some embodiments, support band 104 extends around the entire circumference of collar 114.

Referring to FIG. 1B, catheter 100 may include coupling element 131, which may assist in securing balloon 106. For example, coupling element 131 may be an adhesive that may help secure balloon 106 to outer tube 102. However, coupling element 131 may be used to assist in securing balloon 106 to inner tube 104 or collar 114. Coupling element 131 may be disposed between proximal end 122 of balloon 106 and outer tube 102.

Referring to FIG. 3, balloon 106 may include interior space 117, which may be the sealed volume of space within balloon 106. The volume of interior space 117 may increase as balloon 106 is inflated. For example, interior space 117 may be filled with a medium to cause balloon 106 to inflate. Interior space 117 may be filled with a medium, such as a viscous fluid, causing balloon 106 to inflate since interior space 117 is sealed. The medium may be a viscous fluid, such as a radiopaque contrast, to allow for the imaging of balloon 106 to determine its position during a medical procedure. For example, during a surgical procedure, interior space 117 may be filled with a viscous radiopaque contrasting agent to allow for the location of balloon 106 to be known via medical imaging, such as X-Ray. Further, the medium may include microbubbles to allow for detection of balloon 106 via ultrasound imaging. In some embodiments, the medium may be a 50:50 mixture of iodinated contrast and saline. Balloon 106 may be sealed to prevent the medium from exiting or leaking from balloon 106. For example, balloon 106 may be sealed with an adhesive on proximal end 122 and distal end 124 or by support band 140.

Interior space 117 may be in fluid communication with outer tube 102 via luminal space 127. For example, luminal space 127 may be in communication with inflation lumen 132 via luminal space 127 such that an inflation medium may be introduced into inflation lumen 132 of outer tube 102 to inflate balloon 106. In some embodiments, balloon 106 is inflated with an inflation medium directed into interior space 117 of balloon 106 through luminal space 127 via inflation lumen 132. Due to the inflation medium having a high viscosity, luminal space 127 may be configured to be have a maximum cross-sectional area without increasing outer diameter d2 of outer tube 102. Maximizing luminal space 127 allows for increased flow of the medium entering interior space 117 thereby inflating balloon 106 faster.

Referring to FIGS. 1A-B, catheter 100 may include outer jacket 129. Outer jacket 129 may be disposed over all or a portion of outer tube 102. Outer jacket 129 may be used to maintain a sealed lumen and may be used to cover depressions 136 and/or slots. In some embodiments, proximal end 122 of balloon 106 may be secured to collar 114 via outer jacket 129. In some embodiments, outer jacket 129 extends over a portion of outer tube 102 and onto a portion of collar 114. However, outer jacket 129 may terminate prior to collar 114. Outer jacket 129 may assist in securing balloon 106 to collar 114. For example, a portion of proximal end 122 of balloon 106 may be disposed between inner tube 104 and outer jacket 129. In one embodiment, outer jacket 129 may be a PET sleeve or Polyolefin. Outer jacket 129 may be disposed over approximately 1.5 mm of balloon 106. However, outer jacket 129 may be disposed over between approximately 0.5 mm and approximately 5 mm of balloon 106, between approximately 1 mm and approximately 4 mm of balloon 106, greater than 1.5 mm of balloon 106, or less than 0.5 mm of balloon 106. In one embodiment, the thickness of outer jacket 129 is less than approximately 0.001 inches. In some embodiments, outer jacket 129 is comprised of a soft material on a distal end and stiffer material on a proximal end to increase stiffness, thereby allowing for catheter 100 to be more easily pushed through a lumen or artery.

Referring to FIGS. 3 and 4, distal end 124 of balloon 106 may be secured to catheter 100 via support band 140, 140', an adhesive, or a compressive heat shrink sleeve. Distal end 124 may also be secured to catheter 100 via an outer jacket, similar to outer jacket 129, disposed over distal end 124. The outer jacket, such as a PET sleeve, may be disposed over approximately 1.5 mm of balloon 106. However, the outer jacket may be disposed over between approximately 0.5 mm and approximately 5 mm of balloon 106, between approximately 1 mm and approximately 4 mm of balloon 106, greater than 1.5 mm of balloon 106, or less than 0.5 mm of balloon 106. Catheter 100 may include marker band 119, which may provide the location of balloon 106. For example, marker band 119 may be disposed on inner tube 104 and may indicate the position of the middle of balloon 106. Marker band 119 may be configured to provide the location of the middle of balloon 106 via traditional imaging techniques, such as X-Ray.

Referring to FIGS. 5B and 6, catheter 100 may include a coating solution. Coating solution 203 may be deposited within inner lumen 118 of inner tube 104 and/or within inflation lumen 132 of outer tube 102. Coating solution 203 may be configured to decrease the friction of particles within inner lumen 118. For example, coating solution 203 may be used to deliver compressible embolic particles to a target site with minimal friction between the particles and inner lumen 118.

Coating solution 203 may have a viscosity of 300 cps at 22 degrees Celsius. However, coating solution 203 may have a viscosity of 225 cps at 22 degrees Celsius, 375 cps at 22 degrees Celsius, 200 cps at 22 degrees Celsius, greater than 300 cps at 22 degrees Celsius or less than 300 cps at 22 degrees Celsius. In one embodiment, coating solution 203 is a hydrophilic solution. In another embodiment, coating solution 203 is a hydrophobic solution. In one embodiment, coating solution 203 is biocompatible as outer tube 102 and/or inner tube 104 may be inserted into living tissue. For example, coating solution 203 may be a hydrophilic poly-urethane solution. Coating solution 203 may be diluted with a dilution solution by varying the concentration of the dilution solution in order to change and specify the viscosity of coating solution 203. Specifying the viscosity of coating solution 203 improves the coating performance of coating solution 203 within outer tube 102 and/or inner tube 104. Coating solution 203 may be diluted with a dilution solution by varying the percentage amount of dilution solution in coating solution 203. The percentage of coating solution 203 that is the dilution solution may be between 0% and 50%, 5-15%, 10-40%, or 20%-30%. In some examples, the percentage of coating solution 203 that is dilution solution may be 0%, 5%, 6%, 7%, 8%, 9%, 10%, 11%, 12%, 13%, 14%, 15% 25%, 30%, 30%, 40%, 45%, or 50%. In one embodiment, the percentage of coating solution 203 that is the dilution solution is 50%, thereby substantially diluting coating solution. In another embodiment, the percentage of coating solution 203 that is the dilution solution is 10%, thereby slightly diluting coating solution 203. In one embodiment, a basecoat or primer layer or primer solution is used as an adhesion promoter to enhance the adhesion of coating solution 203 to inner lumen 118 of inner tube 104. The basecoat or primer may have a viscosity of 1000 cps at 22 degrees Celsius.

In one embodiment, coating solution 203 is a thin coating. For example, the solution coating may be a thin coating having a thickness between approximately 1 μm-approximately 25 μm, approximately 6 μm-approximately 20 μm, greater than 25 μm, or less than 1 μm. The thin coating of coating solution 203 may be approximately 2 μm, approximately 7 μm, approximately 10 μm, or approximately 12 μm. The profile of the surface of coating solution 203 within outer tube 102 and/or inner tube 104 may vary. In one embodiment, outer tube 102 and/or inner tube 104 may be treated with a cleaning solution prior to deposition of coating solution 203. For example, inner lumen 118 may be treated with saline or an equivalent to clean inner tube 104 prior to the application of coating solution 203.

In one embodiment, after coating solution 203 has been deposited within outer tube 102 and/or inner tube 104, coating solution 203 may be cured to increase adherence to outer tube 102 and/or inner tube 104. For example, coating solution 203 may be heat cured in, for example, an oven after it has been deposited within outer tube 102 and/or inner tube 104. In one embodiment, coating solution 203 is heat cured at a temperature between 20 degrees Celsius and 90 degrees Celsius, 40 degrees Celsius and 100 degrees Celsius, 60 degrees Celsius and 80 degrees Celsius, or greater than 90 degrees Celsius for a duration of 10 minutes to 120 minutes. For example, coating solution 203 may be heat cured at a temperature of 20 degrees Celsius, 30 degrees Celsius, 40 degrees Celsius, 50 degrees Celsius, 60 degrees Celsius, 70 degrees Celsius, 80 degrees Celsius, 90 degrees Celsius, or 110 degrees Celsius. However, coating solution 203 may be cured at a temperature as high as 150 degrees Celsius. In another embodiment, coating solution 203 may be cured using ultraviolet (UV) light. For example, coating solution 203 may be mixed with a UV-curing agent in order to assist in curing coating solution 203 with UV light.

In one embodiment, subsequent coating solutions may be used after coating solution 203 has been deposited within outer tube 102 and/or inner tube 104. The use of an adhesion promotor may be used to vary the wetting profile of inner lumen 118 of inner tube 104. This may improve the adhesion of coatings subsequent to the application of coating solution 203 within outer tube 102 and/or inner tube 104.

In some embodiments, catheter 100 may be used to deliver fluid or particles to a target site. Catheter 100 may be inserted into a blood vessel via an incision made in the patient's skin. Catheter 100 may extend within the blood vessel until catheter 100 reaches its target site using a guidewire. Once catheter 100 reaches its target site, an inflation medium may be inserted into outer tube 102 via inflation lumen 132. The inflation medium may be used to inflate balloon 106 via luminal space 127. When the inflation medium is used to inflate balloon 106, inner tube 104 may radially shift towards outer tube 102, due to the medium exiting luminal space 127 into interior space 117 of balloon 106. Luminal space 127 may be increased when inner tube 104 radially shifts towards outer tube 102. The inflation medium may be a radiopaque contrasting agent to allow balloon 106 to be located using medical imaging.

Balloon 106 may be inflated to occlude, isolate, or dilate the blood vessel. Once balloon 106 has been inflated, the desired fluid and/or particles may be delivered to the target site via inner lumen 118. Balloon 106 being inflated prevents the fluid and/or particles from flowing to an undesired location. Once the fluid and/or particles have been delivered to the target site, balloon 106 may be deflated by removing the medium from interior space 117 of balloon 106. Once balloon 106 is in a deflated state, catheter 100 may be removed from the blood vessel over the guidewire or may be extended further along the guidewire to a different target site. Balloon 106 may be deflated by removing the medium from within interior space 117. The medium may be removed by applying negative pressure via a syringe to reverse the flow the medium and remove it from interior space 117.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "proximal", "distal", "upper" and "lower" designate directions in the drawings to which reference is made. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A balloon catheter comprising:

an outer tube including a distal end, an inner surface, a longitudinal axis, and an inflation lumen;

an inner tube disposed within the inflation lumen of the outer tube, the inner tube including an outer surface and an inner lumen;

a collar having a proximal end and a distal end, the proximal end of the collar coupled to the inner surface of the outer tube at the distal end of the outer tube such that the collar extends outwardly from the inflation lumen of the outer tube;

a luminal space defined by a space between the outer surface of the inner tube and the collar; and a balloon having a proximal end and a distal end, the proximal end of the balloon being coupled to the collar at the distal end of the outer tube and the distal end of the balloon being coupled to the inner tube, wherein a coupling element is disposed between the outer tube and the balloon such that a distal most end face of the outer tube is directly coupled to the coupling element which is directly coupled to the balloon, wherein the collar includes a slot that extends radially around an outer circumference of the collar, wherein the collar is at least partially disposed around the outer surface of the inner tube and the inner tube partially extends through the slot when the inner tube is disposed within the inflation lumen of the outer tube.

2. The balloon catheter of claim 1, wherein the slot extends longitudinally throughout a majority of a length of the collar.

3. The balloon catheter of claim 1, wherein the slot extends radially approximately 110° around the outer circumference of the collar.

4. The balloon catheter of claim 1, wherein the slot is configured to allow the outer surface of the inner tube to move closer to the inner surface of the outer tube.

5. The balloon catheter of claim 1, further comprising a coating solution deposited on the inner lumen of the inner tube.

6. The balloon catheter of claim 5, wherein the coating solution has a thickness between 1 μm and 25 μm.

7. The balloon catheter of claim 5, wherein the coating solution is biocompatible.

8. The balloon catheter of claim 5, wherein the coating solution is hydrophilic.

9. The balloon catheter of claim 5, wherein the coating solution is hydrophobic.

10. The balloon catheter of claim 5, wherein the coating solution is heat cured between 50 and 90 degrees Celsius after deposition on the inner lumen of the inner tube.

11. The balloon catheter of claim 5, wherein the coating solution is cured using ultraviolet light after deposition on the inner lumen of the inner tube.

12. The balloon catheter of claim 5, wherein the coating solution is cured such that it adheres to the inner lumen of the inner tube.

13. The balloon catheter of claim 6, wherein the coating solution is heat cured for a duration of between 10 minutes and 2 hours.

14. The balloon catheter of claim 5, wherein the coating solution is diluted by varying dilution percentages between 0% and 50%.

15. The balloon catheter of claim 5, wherein a primer solution or a basecoat solution is used as an adhesion promoter between the inner lumen of the inner tube and the coating solution.

16. The balloon catheter of claim 5, wherein a cleaning solution is used to prepare the inner lumen of the inner tube for application of the coating solution.

17. The balloon catheter of claim 16, wherein the cleaning solution is saline or an equivalent.

18. The balloon catheter of claim 1, wherein the outer tube is comprised of nitinol and includes a plurality of slots allowing the outer tube to bend.

19. The balloon catheter of claim 18, wherein a width of each of the plurality of slots decreases along a length of the outer tube from a proximal end of the outer tube to the distal end of the outer tube.

20. The balloon catheter of claim 1, wherein the outer surface of the inner tube engages with the outer tube to lock the inner tube to the outer tube such that rotation of the outer tube causes rotation of the inner tube.

21. The balloon catheter of claim 20 further comprising: an adhesive to lock the inner tube to the outer tube.

22. The balloon catheter of claim 1, wherein the balloon includes an interior space that is in fluid communication with the outer tube through the luminal space of the collar.

23. The balloon catheter of claim 22, wherein the balloon is inflated with an inflation medium directed into the interior space of the balloon through the luminal space.

24. The balloon catheter of claim 1, wherein the collar has an outer diameter that is smaller than an outer diameter of the outer tube.

25. The balloon catheter of claim 1, wherein the collar is comprised of nitinol.

26. The balloon catheter of claim 1, wherein the inner tube is comprised of braided polyimide.

27. The balloon catheter of claim 1, wherein in a deflated state, the balloon has an outer diameter substantially equal to or less than an outer diameter of the outer tube.

28. The balloon catheter of claim 1, wherein the inner tube includes an inner diameter having a diameter substantially equal to or greater than 0.020 inches.

29. The balloon catheter of claim 1, wherein an outer diameter of the outer tube is substantially equal to or less than 0.040 inches.

30. The balloon catheter of claim 1, wherein the inner tube has a wall thickness of approximately 0.003 inches.

31. The balloon catheter of claim 1, further comprising an outer jacket disposed over a portion of the outer tube and a portion of the collar, wherein the outer jacket is configured to be disposed over a portion of the balloon.

32. A balloon catheter comprising:

an outer tube having an outer diameter, an inner surface, a distal end, a longitudinal axis, and an inflation lumen;

an inner tube disposed within the inflation lumen of the outer tube, the inner tube having an inner lumen including a coating solution deposited on the inner lumen;

a collar having an outer diameter that is smaller than the outer diameter of the outer tube, a proximal end, and a distal end, the proximal end of the collar coupled to the inner surface of the outer tube at the distal end of the outer tube such that the collar extends outwardly from the inflation lumen of the outer tube, and the collar having a slot wherein the inner tube is disposed within the slot and partially extends through the slot when the inner tube is disposed within the inflation lumen of the outer tube, and the collar includes a luminal space defined by a space between the inner tube and collar; and a balloon having a proximal end and a distal end, wherein the proximal end of the balloon is coupled to the collar at the distal end of the outer tube and the distal end of the balloon is coupled to the inner tube, and the balloon includes an interior space that is in fluid communication with the outer tube through the luminal space of the collar allowing the balloon to be inflated from a deflated state to an inflated state, wherein a coupling element is disposed between the outer tube and the balloon such that a distal most end face of the outer tube is directly coupled to the coupling element which is directly coupled to the balloon.

* * * * *